(12) United States Patent
Skardal et al.

(10) Patent No.: US 11,993,785 B2
(45) Date of Patent: May 28, 2024

(54) IMMERSION DEPOSITION METHODS AND COMPOSITIONS FOR USE IN THE SAME

(71) Applicant: Wake Forest University Health Sciences, Winston-Salem, NC (US)

(72) Inventors: Aleksander Skardal, Clemmons, NC (US); Casey Cuvan Clark, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 1007 days.

(21) Appl. No.: 16/533,300

(22) Filed: Aug. 6, 2019

(65) Prior Publication Data

US 2020/0048601 A1 Feb. 13, 2020

Related U.S. Application Data

(60) Provisional application No. 62/715,548, filed on Aug. 7, 2018.

(51) Int. Cl.
| | |
|---|---|
| *C12N 5/071* | (2010.01) |
| *B33Y 10/00* | (2015.01) |
| *B33Y 70/00* | (2020.01) |
| *B33Y 80/00* | (2015.01) |
| *C12M 3/00* | (2006.01) |
| *C12N 5/00* | (2006.01) |
| *C12N 13/00* | (2006.01) |
| *G01N 33/50* | (2006.01) |

(52) U.S. Cl.
CPC ............ *C12N 5/0062* (2013.01); *B33Y 10/00* (2014.12); *B33Y 70/00* (2014.12); *B33Y 80/00* (2014.12); *C12M 21/08* (2013.01); *C12N 5/0697* (2013.01); *C12N 13/00* (2013.01); *G01N 33/5088* (2013.01); *C12N 2513/00* (2013.01)

(58) Field of Classification Search
CPC .......................... C12N 5/0062; C12N 5/0697
See application file for complete search history.

(56) References Cited

U.S. PATENT DOCUMENTS

| | | |
|---|---|---|
| 2012/0089238 A1 | 4/2012 | Kang et al. |
| 2012/0114670 A1 | 5/2012 | Land et al. |
| 2016/0167312 A1* | 6/2016 | Feinberg ................. A61L 27/18 264/239 |
| 2017/0107483 A1 | 4/2017 | Pendergraft et al. |
| 2017/0307598 A1 | 10/2017 | Skardal et al. |
| 2018/0000743 A1 | 1/2018 | Welker et al. |
| 2018/0273904 A1 | 9/2018 | Skardal et al. |
| 2018/0291350 A1 | 10/2018 | Murphy et al. |
| 2018/0320141 A1 | 11/2018 | Atala et al. |
| 2018/0348203 A1 | 12/2018 | Skardal |
| 2019/0106673 A1 | 4/2019 | Skardal |
| 2019/0345439 A1 | 11/2019 | Skardal et al. |
| 2020/0108172 A1 | 4/2020 | Skardal et al. |

FOREIGN PATENT DOCUMENTS

| | | |
|---|---|---|
| WO | 2018004906 | 1/2018 |
| WO | 2018005964 | 1/2018 |
| WO | 2018027023 | 2/2018 |
| WO | 2018071354 | 4/2018 |
| WO | 2018081425 | 5/2018 |
| WO | 2019028131 | 2/2019 |
| WO | 2019152767 | 8/2019 |

OTHER PUBLICATIONS

Hinton et al. "Three-dimensional printing of complex biological structures by freeform reversible embedding of suspended hydrogels." Science Advances 1(9) (2015).*
Ling et al. "Bioprinting-Based High-Throughput Fabrication of Three-Dimensional MCF-7 Human Breast Cancer Cellular Spheroids." Engineering 1(2) (2015): 269-274.*
Domansky et al. "Perfused multiwell plate for 3D liver tissue engineering." Lab on a Chip (10)1 (2010) 51-58.*
Boehnke et al. "Assay Establishment and Validation of a High-Throughput Screening Platform for Three-Dimensional Patient Derived Colon Cancer Organoid Cultures." Journal of Biomolecular Screening 21(9) (2016): 931-941.*
Wu et al. "Omnidirectional Printing of 3D Microvascular Networks." Advanced Materials 23(24) (2011): 178-183.*
Eglen et al. Drug Discovery Goes Three-Dimensional: Goodbye to Flat High-Throughput Screening? (2015) Assay and Drug Development Technologies, 13, pp. 262-265 (Year: 2015).*
Wu et al. Omnidirectional Printing of 3D Microvascular Networks (2011) Advanced Healthcare Materials, 23, pp. 178-183. (Year: 2011).*
Zhu et al. Gold Nanocomposite Bioink for Printing 3D Cardiac Constructs (2017) Advanced Functional Materials, 27, pp. 1-12. (Year: 2017).*
Hinton et al. Three-dimensional printing of complex biological structures by freeform reversible embedding of suspended hydrogels (2015) Science Advances 1, pp. 1-10. (Year: 2015).*
Devarasetty et al. "Applications of Bioengineered 3D Tissue and Tumor Organoids in Drug Development and Precision Medicine: Current and Future" BioDrugs, 32(1):53-68 (2018).

(Continued)

Primary Examiner — Kara D Johnson
Assistant Examiner — Maytee Marie Contes De Jesus
(74) Attorney, Agent, or Firm — Myers Bigel, P.A.

(57) ABSTRACT

Provided are methods of preparing organoids and compositions for use in such methods. In some embodiments, a method of depositing a plurality of the cells into a reservoir are provided, the method comprising depositing a gelatin composition into a reservoir; adding a composition comprising a plurality of cells into the gelatin composition, wherein the composition is added into the gelatin composition at a position below the surface of the gelatin composition and at least a portion of the composition and/or plurality of cells are suspended in the gelatin composition; curing at least a portion of the composition comprising the plurality of cells in the gelatin composition; and removing at least a portion of the gelatin composition in the reservoir, thereby depositing the plurality of cells in the reservoir.

19 Claims, 7 Drawing Sheets

(56) References Cited

OTHER PUBLICATIONS

Hinton et al. "Three-dimensional printing of complex biological structures by freeform reversible embedding of suspended hydrogels" Science Advances, 1(9):e1500758 (2015).
Insphero AG "3D InSightTM Human Liver Microtissues" Brochure (2 pages) (2012).
Maloney et al. "Immersion Bioprinting Organoid Constructs in Multi-Well Plates for Increasing Throughput of 3D Drug Screening" Abstract presented at the Summer Scholar Program Research Day on Aug. 8, 2018 (1 page) (publicly disclosed Aug. 8, 2019).
Mazzocchi et al. "In vitro patient-derived 3D mesothelioma tumor organoids facilitate patient-centric therapeutic screening" Scientific Reports, 8(2886):1-12 (2018).

* cited by examiner

IMMERSION DEPOSITION METHODS AND COMPOSITIONS FOR USE IN THE SAME

RELATED APPLICATION DATA

This application claims the benefit of and priority to U.S. Provisional Application No. 62/715,548 filed Aug. 7, 2018, which is incorporated herein by reference in its entirety.

GOVERNMENT SUPPORT

This invention was made with government support under grant number 5UL1TR001420-04 awarded by the National Institutes of Health. The government has certain rights in the invention.

FIELD

The present invention generally relates to methods of preparing organoids and compositions for use in such methods.

BACKGROUND

Drug development has been severely limited due to a lack of preclinical testing in human-based three-dimensional (3D) models, such as bioengineered organoids. Instead, most drug development work has been, and still is, largely performed using two-dimensional (2D) cell cultures and animal models. Neither of these model systems accurately simulates human physiology and biology, and thus they are not always indicative of human responses to drugs and potential toxic effects. By contrast, bioengineered 3D cellular models, or organoids, can be created from human cells. Due to their 3D nature, they can be superior models for drug and toxicity screening studies.

The most common organoid form factor is a spheroid, originally formed in hanging drop cultures. In these cultures, cells are suspended in drops of liquid hanging from a surface. Since the cells have no substrate to adhere to, they aggregate to one another. This technique has been translated to a well plate format via hanging drop plates. These plates make spheroid formation relatively straightforward. Unfortunately, some cell types isolated from fresh tissue or tumor biospecimens do not readily aggregate into spheroids. Instead, they require a matrix in which to reside.

Adoption of 3D organoid systems by the pharmaceutical industry has been relatively slow due to the lack of compatibility that many organoid form factors have with high throughput screening approaches. These approaches typically employ 2D cell cultures in 96-well or 384-well plates. Accurate, consistent, and automated biofabrication of organoids in 96-well or 384-well formats has been difficult. Employing bioprinting, not specifically to create complicated 3D structures, but to deposit simple organoid structures in well plates en masse, may solve this problem. However, the biomaterial bioinks employed currently for bioprinting are typically engineered for continuous extrusion printing of hydrogel filaments, not large numbers of discrete 3D structures in well plates.

SUMMARY

A first aspect of the present invention is directed to a method of depositing a plurality of cells into a reservoir, the method comprising: depositing a gelatin composition into a reservoir (e.g., a well of a well plate); adding a composition comprising a plurality of cells (e.g., a bioink comprising the plurality of cells) into the gelatin composition, wherein the composition is added into the gelatin composition at a position below the surface of the gelatin composition and at least a portion of the composition and/or plurality of cells is/are suspended in the gelatin composition; curing at least a portion of the composition comprising the plurality of cells in the gelatin composition; and removing at least a portion of the gelatin composition from the reservoir, thereby depositing the plurality of cells in the reservoir.

Another aspect of the present invention is directed to a method of printing a plurality of organoids, the method comprising: depositing a gelatin composition into a plurality of reservoirs (e.g., wells of a well plate); adding a composition comprising a plurality of cells (e.g., a bioink comprising the plurality of cells) into the gelatin composition in each reservoir of the plurality of reservoirs, wherein the composition is added into the gelatin composition at a position below the surface of the gelatin composition and at least a portion of the composition and/or plurality of cells is/are suspended in the gelatin composition; curing at least a portion of the composition comprising the plurality of cells in the gelatin composition to form an organoid in each reservoir; and removing at least a portion of the gelatin composition in the plurality of reservoirs, thereby providing the plurality of organoids.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim and/or file any new claim accordingly, including the right to be able to amend any originally filed claim to depend from and/or incorporate any feature of any other claim or claims although not originally claimed in that manner. These and other objects and/or aspects of the present invention are explained in detail in the specification set forth below. Further features, advantages and details of the present invention will be appreciated by those of ordinary skill in the art from a reading of the figures and the detailed description of the preferred embodiments that follow, such description being merely illustrative of the present invention.

DETAILED DESCRIPTION OF EXAMPLE EMBODIMENTS

The present invention is now described more fully hereinafter with reference to the accompanying drawings, in which embodiments of the invention are shown. This invention may, however, be embodied in many different forms and should not be construed as limited to the embodiments set forth herein; rather these embodiments are provided so that this disclosure will be thorough and complete and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a," "an" and "the" are intended to include the plural forms as well, unless the context clearly indicates otherwise.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference in their entirety. In case of a conflict in terminology, the present specification is controlling.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

As used herein, the transitional phrase "consisting essentially of" (and grammatical variants) is to be interpreted as encompassing the recited materials or steps "and those that do not materially affect the basic and novel characteristic(s)" of the claimed invention. See, *In re Herz,* 537 F.2d 549, 551-52, 190 U.S.P.Q. 461, 463 (CCPA 1976) (emphasis in the original); see also MPEP § 2111.03. Thus, the term "consisting essentially of" as used herein should not be interpreted as equivalent to "comprising."

The term "about," as used herein when referring to a measurable value such as an amount or concentration and the like, is meant to encompass variations of ±10%, ±5%, ±1%, ±0.5%, or even ±0.1% of the specified value as well as the specified value. For example, "about X" where X is the measurable value, is meant to include X as well as variations of ±10%, ±5%, ±1%, ±0.5%, or even ±0.1% of X. A range provided herein for a measureable value may include any other range and/or individual value therein.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under." The device may be otherwise oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only unless specifically indicated otherwise.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present invention. The sequence of operations (or steps) is not limited to the order presented in the claims or figures unless specifically indicated otherwise.

As used herein, the terms "increase," "increases," "increased," "increasing," and similar terms indicate an elevation in the specified parameter of at least about 5%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500% or more.

As used herein, the terms "reduce," "reduces," "reduced," "reduction," "inhibit," and similar terms refer to a decrease in the specified parameter of at least about 5%, 10%, 15%, 20%, 25%, 30%, 35%, 40%, 45%, 50%, 55%, 60%, 65%, 70%, 75%, 80%, 85%, 90%, 95%, 97%, or 100%.

"Cells" and "cell" as used in the present invention are, in general, animal cells, particularly mammalian and primate cells, examples of which include, but are not limited to human, dog, cat, rabbit, monkey, chimpanzee, cow, pig, goat. The cells may be differentiated at least in part to a particular cell or tissue type, such as liver, intestine, pancreas, lymph node, smooth muscle, skeletal muscle, central nerve, peripheral nerve, skin, immune system, etc. In some embodiments, the cells are diseased cells. Some cells may be cancer cells, as discussed further below, in which case they optionally may express (naturally, or by recombinant techniques) a detectable compound, as also discussed further below.

"Three dimensional tissue construct" and "organoid" are used interchangeably herein and, as used herein, refer to a composition of live cells, typically in a carrier media, arranged in a three-dimensional or multi-layered configuration (as opposed to a monolayer). An organoid is an artificial, three-dimensional construct created in vitro to mimic or resemble the functionality and/or histological structure of an organ, tissue, or a portion thereof. Suitable carrier media include hydrogels, such as cross-linked hydrogels as described below. In some embodiments, an organoid is formed upon cross-linking (e.g., after UV initiated cross-linking) of the carrier media (e.g., hydrogel). Additional example hydrogels include, but are not limited to, those described in PCT/US2015/055699, PCT/US2016/054607, and PCT/US2017/058531, the contents of each of which are incorporated herein by reference in their entirety. An organoid may comprise one or more (e.g., 1, 2, 3, 4, or more) differentiated cell type(s) depending upon the particular tissue and/or organ being modeled or emulated. Some organoids may comprise diseased cells and/or cancer cells, as discussed further below. When the organoid comprises diseased cells and/or cancer cells, they may include tissue cells and/or may include a tissue mimic without cells, such as an extracellular matrix (or proteins and/or polymers derived therefrom), hyaluronic acid, gelatin, collagen, alginate, etc., including combinations thereof. Thus, in some embodiments, cells are mixed together with an extracellular matrix, or cross-linked matrix, to form the organoid.

In some embodiments, an organoid may be present in and/or formed in a hydrogel comprising thiolated hyaluronic acid (also referred to interchangeably herein as thiol-modified hyaluronic acid), methacrylated collagen (also referred to interchangeably herein as methacrylate-modified collagen), and water.

One or more (e.g., 1, 2, 3, 4, 5, 6, 7, or more) additional components may be present in a hydrogel. For example, in some embodiments, an organoid may be present in a hydrogel comprising methacrylated gelatin (GelMa), heparin sulfate, chondroitin sulfate, alginate sodium salt, unmodified gelatin, elastin, non-thiolated hyaluronic acid, non-methacrylated collagen (e.g., Type I, II, III, and/or IV collagen), one or more components for modifying elastic modulus of the composition, one or more components for cell adhesion profile modification, one or more components for tissue-specific biochemical modification, and/or one or more small molecules (e.g., a small molecule that can has additional cross-linking capability and/or can provide hydrogen bonding and/or non-covalent complexing).

In some embodiments, an organoid may be present in a hydrogel comprising a protein (e.g., an adhesion protein) and/or proteoglycan, optionally a modified protein and/or modified proteoglycan. In some embodiments, the protein and/or proteoglycan may be modified with one or more functional group(s), such as, e.g., modified with a maleimide, that can bind and/or crosslink to thiolated hyaluronic acid, non-thiolated hyaluronic acid, methacrylated collagen, and/or non-methacrylated collagen. In some embodiments, an organoid may be present in a hydrogel comprising fibronectin, heparin, and/or laminin, optionally a modified fibronectin, heparin, and/or laminin (e.g., modified with a maleimide), or other cell adhesion protein(s) and/or or cell adhesion protein peptide derivative(s).

One or more growth factor(s) may be present in a hydrogel. In some embodiments, the hydrogel comprises one or more growth factor(s) that are linked and/or bound by a heparin pendant chain. The one or more growth factor(s) may be appropriate for the particular cells that may be present in and/or added to the hydrogel and/or for the particular tissue substitute and/or organoid being produced. In some embodiments, growth factors and/or other growth promoting proteins may be provided in a decellularized extracellular matrix composition (ECM) from a tissue corresponding to the tissue cells (e.g., decellularized extracellular liver matrix when the live animal cells are liver cells; decellularized extracellular cardiac muscle matrix when the live animal cells are cardiac muscle cells; decellularized skeletal muscle matrix when the live animal cells are skeletal muscle cells; etc.). Additional collagens, glycosaminoglycans, and/or elastin (e.g., which may be added to supplement the extracellular matrix composition), etc., may also be included.

In some embodiments, an organoid may be present in a hydrogel that may be customized to match the biochemical profile of one or more (e.g., 1, 2, 3, 4, 5, or more) tissue(s) (e.g., a tissue found in a mammalian body). In some embodiments, an adhesion protein such as, e.g., one found in a particular tissue, may be synthetically modified to allow for direct coupling to a component in the composition (e.g., the thiolated hyaluronic acid and/or methacrylated collagen). Growth factors may be linked through heparin pendant chains. Fibronectin, laminin, and/or other adhesion proteins may be synthetically modified to have one or more chemical group(s) that crosslink directly into a component in the composition (e.g., the thiolated hyaluronic acid and/or methacrylated collagen), which may allow for tissue-specific customization. In some embodiments, inclusion of covalently linked fibronectin in the composition may have a significant influence in maintaining function of an organoid formed and/or provided in the composition (e.g., a liver organoid).

The cells may be incorporated into a composition and/or hydrogel in any suitable form, including as unencapsulated cells, or as cells previously aggregated as spheroids, or pre-formed organoids (as noted above). Animal tissue cells aggregated or contained in cell spheroids can be produced in accordance with known techniques, or in some cases are commercially available (see, e.g., Insphero A G, 3D *Hepg*2 *Liver Microtissue Spheroids* (2012); Inspherio A G, 3D *InSight™ Human Liver Microtissues*, (2012)).

In some embodiments, an organoid of the present invention comprises cells that are human-derived cells, and, in some embodiments, the organoid comprises cells that consist of human-derived cells. An organoid of the present invention may express and/or produce one or more biomarkers (e.g., 1, 2, 3, 4, or more) that are the same as a biomarker produced by the cells in vivo. For example, liver cells in vivo produce albumin and an organoid of the present invention comprising liver cells may express albumin. In some embodiments, an organoid may express a biomarker in the same amount or in an amount that is ±20%, ±10%, or ±5% of the average amount produced and/or expressed by corresponding cells in vivo. Example biomarkers include, but are not limited to, albumin, urea, glutathione S-transferase (GST) (e.g., α-GST), chemokines (e.g., IL-8, IL-1β, etc.), prostacyclin, SB100B, neuron-specific enolase (NSE), myelin basic protein (MBP), hormones (e.g., testosterone, estradiol, progesterone, etc.), inhibin A/B, lactate dehydrogenase (LDH), and/or tumor necrosis factor (TNF). The cells may be differentiated or undifferentiated cells, but are in some embodiments tissue cells (e.g., liver cells such as hepatocytes, pancreatic cells, cardiac muscle cells, skeletal muscle cells, etc.).

Choice of cells will depend upon the particular organoid being created, and the cells may be labeled with a detectable compound, such as, but not limited to, with a fluorescent compound (e.g., dye, protein, etc.). For example, for a liver organoid, liver hepatocyte cells may be used. For a peripheral or central nerve organoid, peripheral nerve cells, central nerve cells, glia cells, or combinations thereof may be used. For a bone organoid, bone osteoblast cells, bone osteoclast cells, or combinations thereof may be used. For a lung organoid, lung airway epithelial cells may be used. For a lymph node organoid, follicular dendritic lymph cells, fibroblastic reticular lymph cells, leukocytes, B cells, T cells, any myeloid cell (e.g, any myeloid in origin (inclusive of dendritic cells and phagocytes)), any lymphoid in origin cell, or combinations thereof may be used. For a smooth and/or skeletal muscle organoid, smooth muscle cells, skeletal muscle cells, or combinations thereof may be used. For a skin organoid, skin keratinocytes, skin melanocytes, or combinations thereof may be used. The cells may be differentiated upon initial incorporation into the composition, or undifferentiated cells that are subsequently differentiated may be used. Additional cells may be added to any of the compositions and/or hydrogels. In some embodiments, tumor cells and/or immune cells are added to an organoid (e.g., a liver organoid), or an organoid can be primarily comprised of tumor cells, with or without immune cells. In some embodiments, an organoid of the present invention comprises, consists essentially of, or consists of one or more types of immune cell(s), which may be selected from white blood cells, follicular dendritic lymph cells, fibroblastic reticular lymph cells, leukocytes, B cells, T cells, any myeloid cell (e.g, any myeloid in origin (inclusive of dendritic cells and phagocytes)), and/or any lymphoid in origin cell. In some embodiments, the one or more types of immune cell(s) may be collected and/or derived from a lymph node (e.g., a lymph node biospecimen), from bone marrow, and/or from the peripheral blood of a subject.

Cancer cells optionally used in the present invention may be any type of cancer cell, including but not limited to melanoma, carcinoma, sarcoma, blastoma, glioma, breast, lung, and astrocytoma cells, etc. In some embodiments, the cancer cells used in the present invention express N-cadherin, and/or show epithelial to mesenchymal transition. Cancer cells may be cancer cells from any tissue of origin, including but not limited to intestinal (small intestine, large intestine, colon, vermiform appendix), lung, breast, prostate, skin, bone, brain, liver, pancreatic, uterine, cervical, testicular, and ovarian cancer cells, etc.

In some embodiments, cells may be obtained from a subject, such as, for example, a subject or patient undergoing treatment for cancer and/or that has cancer and/or a subject that has a compromised immune system. In some embodiments, cells are tumor cells, such as, e.g., patient biopsy-derived tumor cells, and organoids prepared from such cells may be used to screen potentially effective drugs and/or treatments. Any type of tumor cell may be used in an organoid, device, and/or method of the present invention including, but not limited to, intestinal (small intestine, large intestine, colon, vermiform appendix), lung, breast, prostate, skin, bone, brain, liver, pancreatic, uterine, cervical, testicular, and ovarian tumor cells, etc. Example biopsy-derived tumor organoids include, but are not limited to, mesothelioma, colorectal, appendiceal, lung, melanoma, and sarcoma organoids. In some embodiments, the cells include benign cells (also referred to as non-cancerous cells) obtained from a tissue biopsy. The cells may be differentiated at least in part to a particular cell or tissue type, such as brain, liver, intestine, pancreas, lymph node, smooth muscle, skeletal muscle, central nerve, peripheral nerve, skin, immune system, etc. Biopsy-derived cells (e.g., tumor and/or benign) may be used to form and/or prepare an organoid of the present invention, and the resulting organoid may be prepared and/or used in a method and/or device of the present invention within about 1, 2, 3, 4, 5, 6, 7, or 8 days after the biopsy. In some embodiments, the cells may be labeled with a detectable compound, such as, but not limited to, with a fluorescent compound (e.g., dye, protein, etc.). In some embodiments, an organoid comprising tumor cells, device comprising the same, and/or method of use thereof may be as described in International Application No. PCT/US2017/045277, the contents of which is incorporated herein by reference in its entirety.

In some embodiments, the cells used in a method and/or composition of the present invention are isolated from a tissue and/or tumor in a subject (e.g., from a tissue and/or tumor biopsy obtained from the subject). In some embodiments, the cells used in a method and/or composition of the present invention are a type of cell that doesn't readily and/or easily aggregate into a spheroid such as, e.g., using a hanging drop method.

In some embodiments, an organoid of the present invention is not prepared from and/or does not comprise cells from an immortalized cell line. Organoids of the present invention may comprise and/or be prepared using high functioning cells, such as, but not limited to, primary cells and/or stem cells, e.g., induced pluripotent stems and/or differentiated iPS-derived cells.

In some embodiments, an organoid of the present invention comprises a core comprised of live tumor cells; and a shell surrounding (e.g., encapsulating) the core, the shell comprised of live immune cells and/or live benign cells (e.g., tissue cells, non-cancerous cells, etc.). The benign cells may be obtained and/or derived from a subject, such as, e.g., a tissue in the subject, and optionally from the same subject as the tumor cells and/or immune cells. In some embodiments, the live benign cells may be obtained and/or derived from a tissue biopsy and/or may be tissue specific. An organoid comprising live benign cells may be separate (e.g., separately formed and/or present in a different chamber of a device) from an organoid comprising live tumor cells and/or immune cells.

When cells (e.g., immune cells, tumor cells, and/or benign cells) are obtained from a subject such as, e.g., from a tissue sample and/or tumor biopsy from a subject, different cell populations may be separated to provide one or more separate populations of cells, and one or more of the separate populations of cells may be labeled and/or used to prepare an organoid as described herein. Methods of separating different populations of cells are known to those of skill in the art and any suitable method may be used, such as, but not limited to, fluorescence activated cell sorting (FACS). When two or more populations of cells are labeled, the two or more populations of cells may have a different detectable signal. In some embodiments, the tissue sample and/or tumor biopsy may be genetically sequenced in part or in full in order to identify mutations, and any mutations identified may indicate and/or suggest one or more compound(s) of interest for therapeutic purposes for the subject (e.g., immune system modulating activity and/or anti-tumor activity). A method of the present invention may comprise screening the one or more compound(s) of interest that were identified in the genetic sequencing and contacting each of the one or more compound(s) of interest and/or a combination thereof to the organoid prepared using the cells from the tissue sample. An organoid of the present invention may have the same or substantially the same heterogeneity as a tissue and/or tumor found in vivo in a subject.

The one or more populations of cells (each of which may optionally be labeled) may be combined in any suitable manner. In some embodiments, the one or more populations of cells may be added to the same common media and/or hydrogel. In some embodiments, the one or more populations of cells may be used to form an organoid as described herein that is encapsulated by a hydrogel of the present invention. One or more different populations of cells in an organoid of the present invention may be present in substantially the same (e.g., within about ±20%) amount as the amount of cells in that population in a tissue and/or tumor in vivo. In some embodiments, when cells have been obtained from a tissue sample from a subject, sorted and/or labeled, the different populations of cells are combined in substantially the amount as the amount present in the tissue sample.

In some embodiments, at least two (e.g., 2, 3, 4, 5, 6, 7, 8, or more) different organoids are formed with cells obtained and/or derived from a single subject (e.g., using one or more biopsies from the subject), with at least one organoid comprising live tumor cells from a tumor biopsy from the subject and at least one separate organoid comprising live immune cells and/or live benign (e.g. liver) cells from the subject. In some embodiments, at least two (e.g., 2, 3, 4, 5, 6, 7, 8, or more) organoids are formed with cells obtained and/or derived from a single subject (e.g., using one or more biopsies from the subject), with at least one organoid comprising live tumor cells from a tumor biopsy from the subject and optionally comprising immune cells from the subject, and at least one separate organoid comprising live benign cells from the subject that are the same tissue type as the live tumor cells and optionally comprising immune cells from the subject. In some embodiments, a tissue biopsied from a subject may be used to prepare one or more organoids of the present invention, optionally with cells obtained from a 2 mm×2 mm minced tissue. In some embodiments, an organoid of the present invention may be useful as a tumor model and/or as an immune system model. For example, the organoid may useful for evaluating immunological activity and/or modulating the immune system and/or useful for screening one or more cancer therapies and/or immunotherapies.

In some embodiments, an organoid is about 100 µm or 200 µm to about 350 or 500 µm in diameter in at least one dimension, such as, for example, about 100, 150, 200, 250, 300, 350, 400, 450, or 500 µm in at least one dimension. In some embodiments, an organoid is about 1 µL to about 20 µL in volume such as, for example, about 1, 2, 3, 4, 5, 6, 7, 8, 9, 10, 11, 12, 13, 14, 15, 16, 17, 18, 19, or 20 µL in volume. The organoid may comprise about 1,500, 2,000, or 5,000 to about 10,000, 25,000, or 50,000 cells in total or about 1,000, 5,000, 10,000, or 50,000 to about 75,000, 100,000, 150,000, 250,000, 500,000, 750,000, 1,000,000, 50,000,000, or 100,000,000 cells in total. In some embodiments, an organoid of the present invention may comprise about 1, 2, or 5 million to about 10, 50, or 100 million cells per mL. In some embodiments, an organoid of the present invention may comprise about 10 million cells per mL. An organoid of the present invention may be in any suitable shape, such as, e.g., any three-dimensional shape or multi-layered shape. In some embodiments, an organoid of the present invention is in the form of a spheroid. In some embodiments, an organoid of the present invention may be self-organized in a suspension or medium (e.g., a cross-linked hydrogel).

"Subjects" as used herein are, in general, human subjects, although aspects of the invention may be implemented with other animal subjects, particularly mammalian subjects (e.g., dogs, cats, horses, goats, and sheep) for veterinary and/or research purposes. Subjects may be male or female and of any age, including infant, juvenile, adolescent, adult, and geriatric.

"Growth media" and "culture media" are used interchangeably herein and may be any natural or artificial growth media (typically an aqueous liquid) that sustains the cells used in carrying out the present invention. Examples include, but are not limited to, an essential media or minimal essential media (MEM), or variations thereof such as Eagle's minimal essential medium (EMEM) and Dulbecco's modified Eagle medium (DMEM), as well as blood, blood serum, blood plasma, lymph fluid, etc., including synthetic mimics thereof. In some embodiments, the growth media includes a pH color indicator (e.g., phenol red).

"Test compound", "candidate compound" and "compound of interest" are used interchangeably herein and may be any compound or agent for which a pharmacological or physiological activity is to be determined such as, e.g., for which a pharmacological or physiological activity on a cell or tissue (e.g., a cardiac tissue) and/or an interaction between two test compounds/agents is to be determined. For demonstrative purposes, isoproterenol, quinidine, propranolol, and epinephrine are example test compounds. However, any compound/agent may be used including organic compounds such as, but not limited to, proteins, peptides, nucleic acids, and/or small organic compounds (aliphatic, aromatic, and mixed aliphatic/aromatic compounds). Candidate compounds may be generated by any suitable techniques, including randomly generated by combinatorial techniques, and/or rationally designed based on particular targets. Where a drug interaction is to be studied, two (or more) test compounds may be administered concurrently, and one (or both) may be known compounds, for which the possible combined effect is to be determined. In some embodiments, the test compound is a metal, such as, but not limited to, aluminum, lead, etc. In some embodiments, the test compound is a heavy metal, such as, but not limited to, arsenic, cadmium, chromium, lead, and/or mercury. In some embodiments, the test compound is a pesticide. In some embodiments, the test compound is a chemotherapy agent and/or an immunotherapy agent. In some embodiments, an immunotherapy agent modulates and/or affects one or more activities and/or components of a subject's immune system. In some embodiments, the immunotherapy agent may be vemurafenib, ipilimumab, nivolumab, and/or pembrolizumab. In some embodiments, the test compound is a check point inhibitor (e.g., PD-1 inhibitor, CTLA-4 inhibitor, etc.). In some embodiments, the test compound comprises engineered immune cells such as, e.g., CAR T cells.

"Detectable compound" as used herein may be a fluorescent compound (e.g., a fluorescent protein (e.g., red fluorescent protein, green fluorescent protein, etc.)), an antigenic protein or peptide to which an antibody coupled to an enzyme, fluorescent, or radioactive group, or other label, will specifically bind, or any other suitable detectable compound. The detectable compound may be one naturally occurring in a cell (e.g., a cancer cell, such as, e.g., a cell marker protein that is expressed at higher levels in cancer cells than non-cancer cells), or one inserted into a cell by genetic engineering/recombinant DNA techniques (i.e., heterologous). In some embodiments, the detectable compound is a quantum dot (QD), a fluorescent organic dye, and/or a fluorescent protein. In some embodiments, a cell may express (naturally, or by recombinant techniques) a detectable compound.

A detectable compound may be any suitable compound that provides and/or generates a detectable signal that allows for differentiation and/or identification of a cell and/or cell population. A detectable signal may be provided and/or generated by one or more detectable compounds associated with a cell. In some embodiments, the detectable signal is a signal (e.g., an optical and/or electrical signal) that is generated by one or more detectable compounds (e.g., chemicals, proteins, etc.) associated with (e.g., applied to, attached to, bound to, compounded with, etc.) a cell. A detectable signal may be optically and/or electronically detectable, which may be perceived visually with the human eye and/or electronically read, detected, and/or obtained using methods known to those of skill in the art. In some embodiments, a detectable signal for a cell and/or cell population may be the absence of a signal (i.e., no detectable signal such as, e.g., no detectable fluorescence from the cell). In some embodiments, a detectable signal for a cell and/or cell population is a fluorescence signal.

A device and/or system of the present invention may comprise a detector (e.g., a camera) and/or an excitation source (e.g., an excitation light source). The detector may detect and/or image the detectable signal from a cell and/or cell population. The excitation source may be used to and/or may generate the detectable signal, such as, e.g., may be used to provide and/or generate light which may cause a detectable compound to fluoresce and thereby provide and/or generate the detectable signal.

In some embodiments, at least a portion of a device (e.g., a microfluidic device) of the present invention is transparent. For example, in some embodiments, the top and/or bottom substrate of the device may be transparent and/or the hydrogel present in the device may be transparent. The device may comprise a detector (e.g., a camera) operatively associated with the device. The detector may be operatively associated with one or more of the chambers of the device. In some embodiments, the detector is provided above and/or below the device and an excitation source may be provided above and/or below the device. In some embodiments, the detector comprises the excitation source (e.g., the light such as the flash and/or LED of a camera). The detector may be configured for detecting (e.g., imaging) cells in one or more chambers of the device. In some embodiments, the device may include a detector (e.g., a LED/CCD detector) positioned to allow images of labeled cells in contact with one or more chambers of the device to be imaged and/or quantified in real time. In some embodiments, the detector may capture images (e.g., fluorescent images) at predetermined intervals and/or may capture images and/or incidences of colonization, migration, and/or growth of labeled cells in and/or from an organoid present in the one or more chambers, which may enable real-time observation and/or quantitation of cells in the organoid and/or their growth, metastasis, migration, and/or the like.

A composition comprising a plurality of cells may be referred to herein as a "bioink" or a "bioink composition" (both of which are used interchangeably herein), and the plurality of cells may comprise two or more live cell(s). As noted above, the cells may be animal cells (e.g., bird, reptile, amphibian, etc.) and in some embodiments are mammalian cells (e.g., dog, cat, mouse, rat, monkey, ape, human). The cells may be differentiated or undifferentiated cells, but are in some embodiments tissue cells (e.g., liver cells such as hepatocytes, pancreatic cells, cardiac muscle cells, skeletal muscle cells, etc.). However, the compositions of the present invention are not limited to use as a bioink and/or in bioprinting and may be useful in other areas, such as, for example, for encapsulation and/or delivery of an agent. In some embodiments, cells present in a bioink prior to deposition according to embodiments of the present invention are not aggregated. In some embodiments, cells present in a bioink prior to deposition according to embodiments of the present invention are aggregated such as, e.g., aggregated in the form of a spheroid or pre-formed organoid.

According to some embodiments of the present invention provided are methods of depositing cells. In some embodiments, methods of the present invention may be used to prepare one or more organoid(s).

In some embodiments, a method of depositing a plurality of the cells into a reservoir comprises: depositing a gelatin composition into a reservoir; adding a composition comprising a plurality of cells (i.e., bioink) into the gelatin composition, wherein the composition is added into the gelatin composition at a position below the surface of the gelatin composition and at least a portion of the composition and/or plurality of cells are suspended in the gelatin composition; curing at least a portion of the composition comprising the plurality of cells in the gelatin composition; and removing at least a portion of the gelatin composition in the reservoir, thereby depositing the plurality of cells in the reservoir.

The compositions (e.g., the gelatin composition and/or the bioink) may be deposited and/or added into the reservoir using methods known to those of skill in the art and include, but are not limited to, inserting, injecting, adding, pouring, printing, and/or the like such a composition into the reservoir. In some embodiments, the gelatin composition and/or the bioink is deposited and/or added into the reservoir using a syringe, pipette, needle, and/or printer (e.g., via a printhead). In some embodiments, the gelatin composition and/or bioink are added into a reservoir using a syringe and/or printer. Exemplary printers include, but are not limited to, bioprinters commercially available from Allevi and/or bioprinters commercially available from CELLINK® such as, e.g., the INKREDIBLE+™ 3D bioprinter.

The reservoir may be any suitable reservoir or container that holds the gelatin composition and composition comprising the plurality of cells. In some embodiments, the reservoir is a well of a well plate such as, but not limited to, a well in a 96-well plate or 384 well-plate.

In some embodiments, about 25, 50, 75, 100, or 125 μL to about 145, 150, 200, 250, 300, 350, or 400 μL of the gelatin composition is deposited into the reservoir. In some embodiments, about 100 or 150 μL to about 250 or 300 μL of the gelatin composition is deposited into the reservoir. In some embodiments, about 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, or 400 μL of the gelatin composition is deposited into the reservoir. In some embodiments, about 200 μL of the gelatin composition is deposited into the reservoir.

The gelatin composition may comprise gelatin at a concentration of about 1, 2, 3, 4, 5, 6, 7, 8, 9, or 10 mg/mL to about 11, 12, 13, 14, 15, 16, 17, 18, 19, or 20 mg/mL. In some embodiments, gelatin is present in the gelatin composition in an amount of about 1, 2, 3, 4, 5, 6, 7, 8, 9, 10, 11, 12, 13, 14, 15, 16, 17, 18, 19, or 20 mg/mL. In some embodiments, gelatin is present in the gelatin composition in an amount of about 10 mg/mL. The gelatin composition may be prepared by dissolving gelatin into water, optionally using heat. Thus, the gelatin composition may be a gelatin solution and/or the gelatin composition comprises dissolved gelatin (e.g., at a concentration of about 1 to about 20 mg/mL). In some embodiments, after deposition of a gelatin composition into a reservoir, the gelatin composition is allowed to cool to about room temperature and/or to solidify before a bioink is added into the gelatin composition.

In some embodiments, a gelatin composition of the present invention includes a curing agent. Exemplary curing agents include, but are not limited to, initiators such as, e.g., thermal initiators and/or photoinitiators. In some embodiments, the curing agent initiates and/or catalyzes a crosslinking reaction in the gelatin composition and/or bioink such as, but not limited to a crosslinking reaction involving unreacted methacrylate groups (e.g., unreacted metacrylate groups on the methacrylated collagen). Example photoinitiators include, but are not limited to, 4-(2-hydroxyethoxy)phenyl-(2-hydroxy-2-propyl)ketone, 2-hydroxy-4'-(2-hydroxyethoxy)-2-methylpropiophenone, and/or IRGACURE® commercially available from BASF.

A curing agent (e.g., a photoinitiator) may be present in a composition of the present invention (e.g., a gelatin composition and/or composition comprising a plurality of cells) in an amount from about 0.01% to about 0.1% or 1% w/v of the composition. In some embodiments, the curing agent is present in the composition in an amount of about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, or 1% w/v of the composition. In some embodiments, a gelatin composition and/or bioink comprises a curing agent (e.g., a photoinitiator) in an amount of about 0.1% w/v of the composition. In some embodiments, both the gelatin composition and bioink comprise a curing agent that may be the same or different and/or in the same or a different concentration. In some embodiments, the gelatin composition and bioink comprise at least one curing agent that is the same, optionally at about the same concentration. In some embodiments, the gelatin composition and bioink comprise a curing agent in approximately the same concentration or the gelatin composition comprises the curing agent in a greater amount than the bioink.

The gelatin composition and/or bioink may be extrudable. For example, in some embodiments, the gelatin composition and/or bioink may be extrudable from a syringe and/or bioprinter. In some embodiments, the gelatin composition and/or bioink may be extruded with an applied mechanical stress in a range from about 5 kPa to about 80 kPa. In some embodiments, the gelatin composition and/or bioink may be extruded with an applied mechanical stress of about 5, 10, 15, 20, 25, 30, 35, 40, 45, 50, 55, 60, 65, 70, 75, or 80 kPa.

In some embodiments, the gelatin composition has a viscosity prior to, during, and/or after deposition of about 0.01 Pascals*seconds (Pa·s) to about 0.05, 0.1, 0.5, 1, 5, 10, 15, or 20 Pa·s. In some embodiments, the gelatin composition has a viscosity prior to, during, and/or after deposition of about 0.01, 0.05, 0.1, 0.5, 1, 2, 3, 4, 5, 6, 7, 8, 9, 10, 11, 12, 13, 14, 15, 16, 17, 18, 19, or 20 Pa·s.

The gelatin composition may have a viscosity and/or elastic modulus that is compatible with a bioink. In some embodiments, the gelatin composition has an elastic modulus that does not compress and/or squeeze out the bioink after addition of the bioink and/or after removal of a device used to add the bioink syringe, needle, print head, etc.). A gelatin composition may have an elastic modulus of about 5 Pa to about 15 Pa at about 1% to about 100% strain. In some embodiments, a gelatin composition may have an elastic modulus of about 5, 6, 7, 8, 9, 10, 11, 12, 13, 14, or 15 Pa at about 1%, 5%, 10%, 20%, 30%, 40%, 50%, 60%, 70%, 80%, 90%, or 100% strain. In some embodiments, the gelatin composition has an elastic modulus that allows for and/or provides the bioink in a substantially spherical form after addition of the bioink and/or after removal of a device used to add the bioink. "Substantially spherical" as used herein refers to a form that upon visible inspection more closely resembles a sphere rather than a disc-shape (i.e., a flat circular shape). In some embodiments, a gelatin composition and bioink used in the gelatin composition have substantially the same viscosity and/or elastic modulus. "Substantially the same" as used herein in reference to the viscosity and/or elastic modulus of a gelatin composition and bioink refer to two compositions that have a viscosity or elastic modulus within an order of magnitude of each other. For example, in some embodiments, a gelatin composition may have an elastic modulus of about 10 Pa at low strain or about 1-100% strain and a bioink has an elastic modulus of about 3 Pa to about 4 Pa at low strain or about 1-100% strain. In some embodiments, a gelatin composition and bioink are compatible in that the bioink can be deposited and/or added into the gelatin composition and the bioink maintains a substantially spherical form, optionally until at least a portion of the bioink is crosslinked.

The bioink may be a carrier media such as, but not limited to, a hydrogel (e.g., a cross-linked hydrogel) as described above. In some embodiments, exemplary bioinks include, but are not limited to, those described in PCT/US2015/055699, PCT/US2016/054607, and PCT/US2017/058531, the contents of each of which are incorporated herein by reference in their entirety. In some embodiments, the bioink comprises thiolated hyaluronic acid and methacrylated collagen (e.g., methacrylated Type 1 collagen). In some embodiments, the bioink may be cross-linked such as, for example, upon exposure to light (e.g., ultra violet (UV) light).

In some embodiments, about 1, 5, 10, or 15 μL to about 20, 25, 30, 35, 40, or 50 μL of the bioink is added into the gelatin composition. In some embodiments, about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 μL of the bioink is added into the gelatin composition. In some embodiments, the location at which the bioink is added into the gelatin composition and/or the volume of the gelatin composition is sufficient to substantially submerge (i.e., at least 90% or more) the bioink in the gelatin composition. In some embodiments, the location at which the bioink is added into the gelatin composition and/or the volume of the gelatin composition is sufficient to completely submerge (i.e., 100%) the bioink in the gelatin composition. In some embodiments, the bioink is added into the gelatin composition at approximately the center of the gelatin composition in the reservoir.

Curing the bioink may be accomplished using methods known to those of skill in the art. In some embodiments, a bioink of the present invention is cured and/or cross-linked by exposing the bioink to light (e.g., ultraviolet light, visible light and/or blue light), optionally in the presence of a photoinitiator.

In some embodiments, a portion or all of the gelatin composition may be removed from the reservoir after the bioink is added and optionally cured, which results in at least a portion of the plurality of cells remaining in the reservoir. In some embodiments, at least about 10%, 15%, 20%, 25%, 30%, 35%, 40%, 45%, 50%, 55%, 60%, 65%, 70%, 75%, 80%, 85%, 90%, 95%, 98%, or 100% of the gelatin composition is removed from the reservoir after the bioink is added and optionally cured. In some embodiments, at least about 50% of the gelatin composition is removed after the bioink is added and cured.

The gelatin composition may be removed from the reservoir by adding a solution (e.g., water and/or cell culture media) into the reservoir to wash away at least a portion of the gelatin composition. In some embodiments, the gelatin composition is removed by placing a volume of a solution (e.g., cell culture media), optionally warmed, on top of the gelatin composition. The solution may at least partially dilute and/or dissolve the gelatin composition. The solution may be removed (e.g., aspirated with a pipette) and optionally more solution may be added to further remove the gelatin composition. In some embodiments, a solution may be added and removed one or more (1, 2, 3, 4, 5, 6, or more) times, optionally until the desired amount of gelatin composition is removed. In some embodiments, after removing a portion of the gelatin composition, cell culture media is added into the reservoir comprising a plurality of cells and/or organoid.

A method of the present invention may comprise depositing a gelatin composition into one or more (e.g., 1, 5, 10, 50, 100, 150, 200, 250, 300, 350, 400 or more) reservoirs and adding a bioink into the gelatin composition in each reservoir of the one or more reservoirs. The bioink added into the gelatin composition in each respective reservoir may be the same or different. In some embodiments, the bioink added into each respective reservoir is the same (i.e., comprises the same components and cells types). In some embodiments, the bioink added into each respective reservoir is different in that the bioink comprises different components and/or different cells types.

According to some embodiments provided is a method of printing a plurality of organoids, the method comprising: depositing a gelatin composition into a plurality of reservoirs; adding a composition comprising a plurality of cells (i.e., a bioink) into the gelatin composition in each reservoir of the plurality of reservoirs, wherein the composition is added into the gelatin composition at a position below the surface of the gelatin composition and the composition and/or plurality of cells are suspended in the gelatin composition; curing the composition comprising the plurality of cells in the gelatin composition to form an organoid in each reservoir; and removing at least a portion of the gelatin composition in the plurality of reservoirs, thereby providing the plurality of organoids.

In some embodiments, when a method of the present invention is used to provide (e.g., deposit) a plurality of cells in two or more reservoirs, then less than about 20% (e.g., less than about 15%, 10%, 5%, or 1%) of the two or more reservoirs are connected such as, e.g., fluidically connected and/or connected by a filament of the bioink, after adding the bioink into the gelatin composition in each reservoir. For example, a bioink (e.g., one that is partially crosslinked) can be printed and as the printhead is pulled out of a first reservoir, the bioink may stay connected (fully or partially) to the printhead, which can either leave no organoid in the first reservoir or can leave a filament that connects the first reservoir to a second reservoir when the printhead travels to the second reservoir, thereby connecting the reservoirs. A method of the present invention may avoid and/or reduce these problems. In some embodiments, a gelatin composition of the present invention holds a majority or all of a bioink in a reservoir. In some embodiments, a gelatin composition of the present invention holds at least about 75%, 80%, 85%, 90%, 95%, 98%, 99%, or 100% of a bioink in a reservoir and submerged in the gelatin composition.

In some embodiments, when a method of the present invention is used to provide (e.g., deposit) a plurality of cells in two or more reservoirs, then greater than about 80% (e.g., greater than about 85%, 90%, 95%, 98%, or 99%, or about 100%) of the two or more reservoirs include a plurality of cells, after adding the bioink into the gelatin composition in each reservoir.

In some embodiments, a method of the present invention may comprise and/or provide one or more (e.g., 1, 5, 10, 50, 100, 150, 200, 250, 300, 350, 400, or more) organoids that are viable for at least 1, 2, 3, 4, or more weeks. In some embodiments, one or more of the organoids may be viable and may comprise at least about 75% or more (e.g., about 80%, 85%, 90%, 95%, 98%, or more) living cells based on the average number of cells present in the organoid at 1, 2, 3, 4, or more weeks. The organoids may be generated by differentiation from a common cell sample (e.g., a sample such as a tissue sample collected from a subject). One or more of the organoids may comprise cells in proportions similar to the proportions of cells present in the corresponding native (e.g., human) tissue. In some embodiments, at least one of the organoids comprises metastatic and/or malignant cells. In some embodiments, a function and/or property of the organoid may be determined and/or measured and compared to the function and/or property of a corresponding native tissue (e.g., a property of a brain organoid may be measured and compared to the same property of a brain tissue in a subject). In some embodiments, a function and/or property of the tissue and/or organoid may be similar to the function and/or property of a corresponding native tissue.

As described herein, cells and/or a cell sample may be used in a method of the present invention to form an organoid of the present invention. Methods of the present invention can provide a viable organoid. In some embodiments, a method of the present invention can achieve a take rate of at least 50% or more such as, e.g., about 50%, 55%, 60%, 65%, 70%, 75%, 80%, 85%, 90%, 95%, 98%, or more. For example, a 90% take rate means that 90% of the time a viable organoid or plurality of organoids (e.g., an organoid set) is achieved and/or provided by a method of the present invention. That is, for a 90% take rate, 9 out of 10 cell samples (e.g., tumor cell samples) yield a viable organoid or plurality of organoids when prepared according to a method of the present invention. The organoid or plurality of organoids may be used in another method of the present invention and/or diagnostics. In some embodiments, the cells and/or cell sample may be from a tumor, such as, e.g., a tumor biopsy.

A method of the present invention may provide a plurality of organoids such as, e.g., about 5, 10, 50, 100, 150, 200, 250, 300, 350, 400, or more organoids. In some embodiments, a printer is used to add the bioink into the gelatin composition. A method of the present invention may provide the plurality of organoids in less than about 60 minutes such as, e.g., less than about 55, 50, 45, 40, 35, 30, 25, 20, 15, 10, 5, or 2 minutes. In some embodiments, a method of the present invention may form a plurality of organoids having a substantially uniform (i.e., within about ±20%) shape and/or diameter in at least one dimension.

In some embodiments, a method of the present invention and/or an organoid prepared therefrom are used in a high throughput assay such as, e.g., a high throughput drug screening.

Some embodiments of the present invention include an array and/or device comprising the plurality of organoids prepared according to a method of present invention.

The foregoing and other aspects of the invention are explained further in the following examples.

EXAMPLES

Example 1—Immersion Bioprinting Organoid Constructs in Multi-Well Plates for Increasing Throughput of 3D Drug Screening A technique was designed to bioprint tissue organoids into multi-well plates to increase throughput of 3D drug screening.

Materials and Methods: HepG2, Caco2, and A549 cells were cultured using standard protocols. Cells were printed with the CELLINK® INKREDIBLE™ printer. Two hydrogel bioinks comprised of natural extracellular matrix components were tested. Images of live/dead-stained were taken with a macro-confocal microscope to assess viability, while MTS assays were performed to quantify mitochondrial metabolism of the cells over time.

Figure 1A:
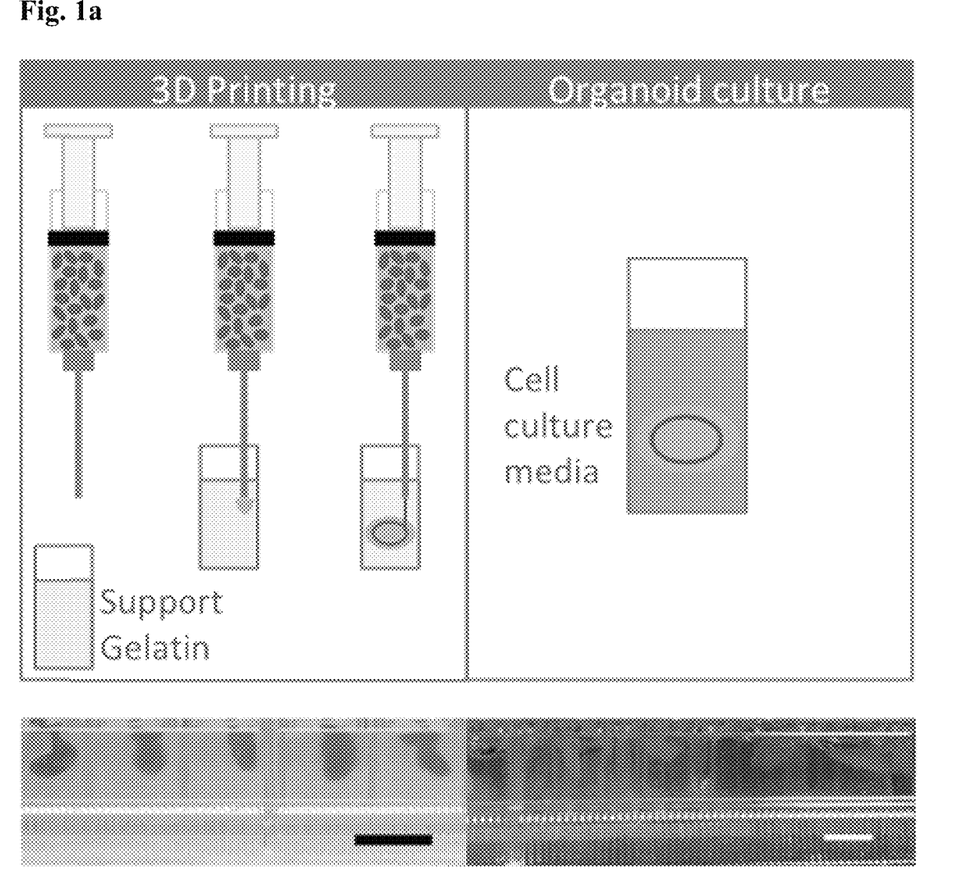
FIG. 1a shows a schematic of an immersion printing process according to some embodiments of the present invention. Below the 3D printing schematic (left schematic) is an image of wells including a bioink immersed in a gelatin composition. After printing completion, the gelatin composition is removed and replaced with cell culture media (right schematic) and below the right schematic is an image of wells after removal of the gelatin composition with the bioink in cell culture media.
Figure 1B:
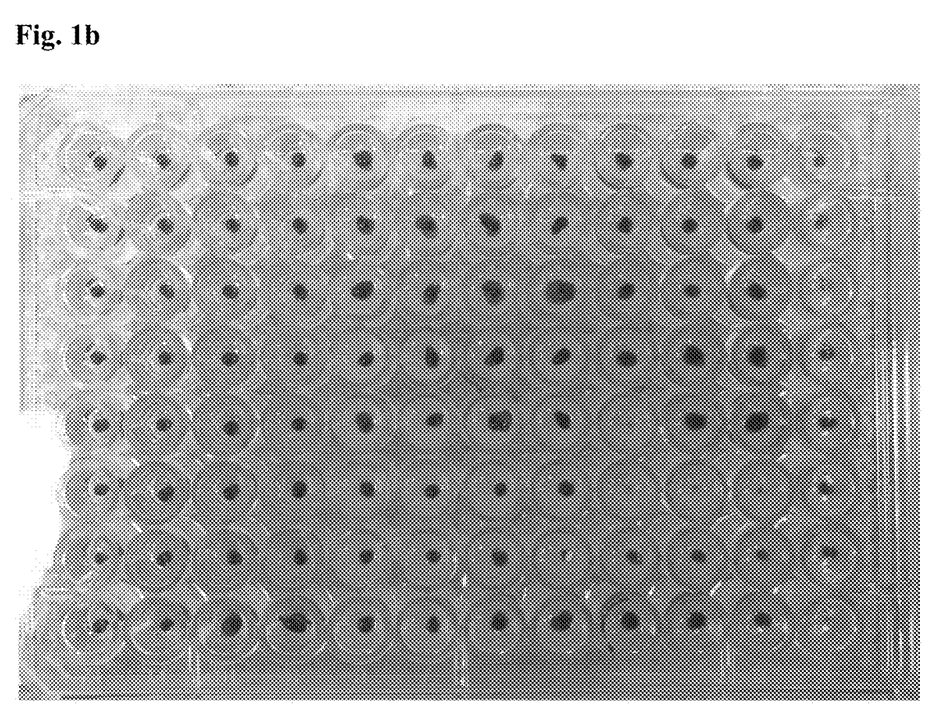
FIG. 1b is an image of printed thiolated hyaluronic acid (HA) and methacrylated collagen gel immersed in a gelatin composition according to some embodiments of the present invention.
Figure 1C:
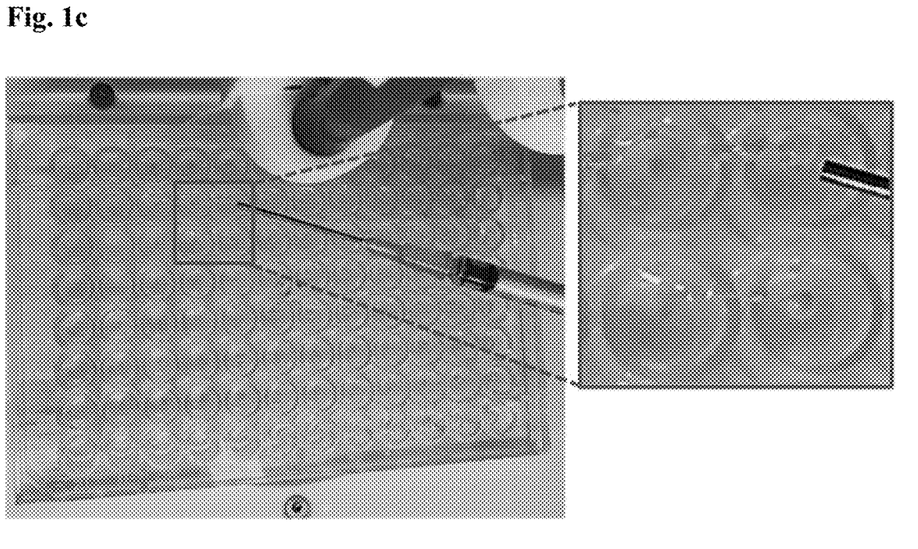
FIG. 1c is an image of printed HYSTEM® gel (thiolated HA, thiolated gelatin and PEGDA) immersed in a gelatin composition with the inset showing the crosslinked gel connecting two wells according to some embodiments of the present invention.
Figure 1D:
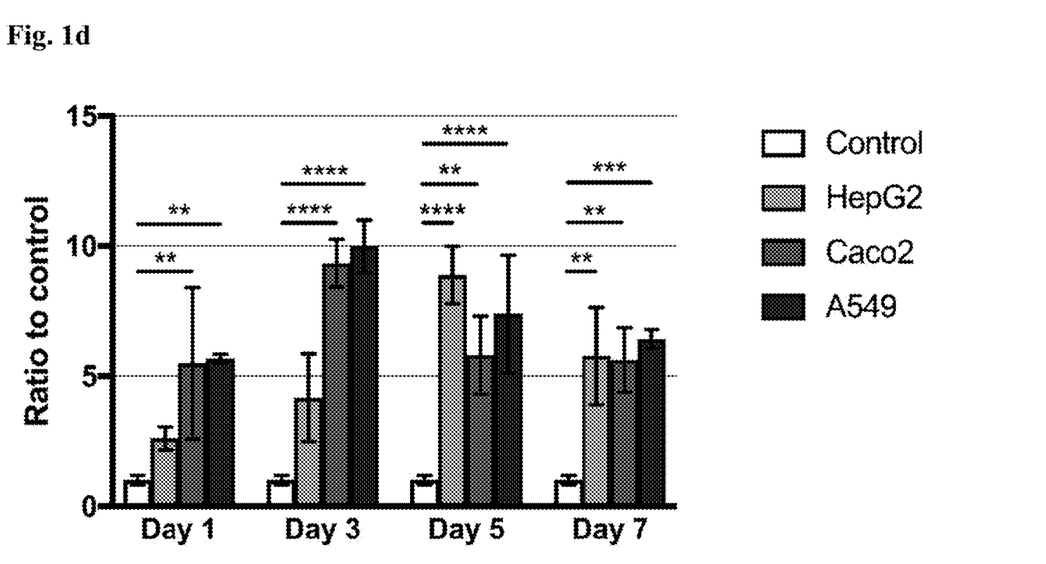
FIG. 1d is a graph of the results from a MTS assay of cells at day 1, 3, 5, and 7 time points.
Figure 1E:
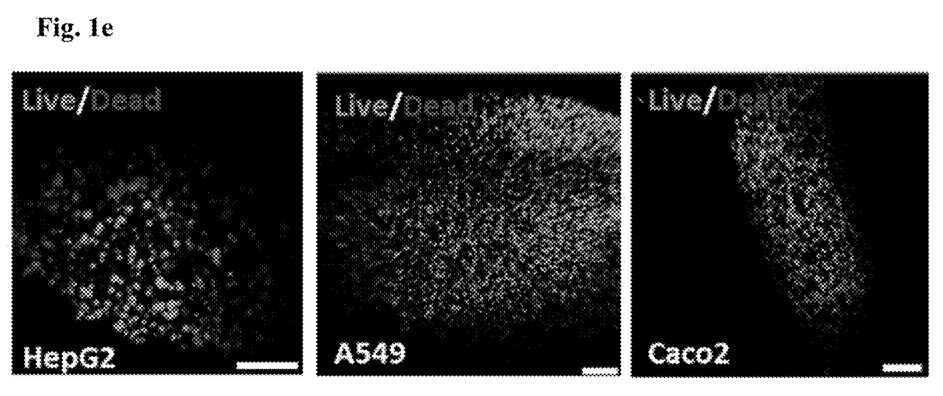
FIG. 1e are images of live/dead staining of organoids (scale bar=200 microns).

Results and Discussion: As seen in FIG. 1a, the organoids were printed into a 96-well plate that contains a support gelatin bath. Once completed, the gelatin was removed, leaving the organoids in tissue culture media. To demonstrate the flexibility of the approach, we printed with two different bioinks: a thiolated hyaluronic acid and methacrylated collagen hydrogel and the commercially available HYSTEM® hydrogel (thiolated hyaluronic acid, thiolated gelatin, and PEGDA) (FIGS. 1b and 1c). The HYSTEM® gel was crosslinking midprint shown by the red box in FIG. 1c, leading to problems during the print process. Organoids were cultured for 7 days and a MTS assay and live/dead staining was taken at the day 1, 3, 5, and 7 time points (FIGS. 1d and 1e) demonstrating high viability immediately following bioprinting and over time in culture.

Example 2

Figure 2:
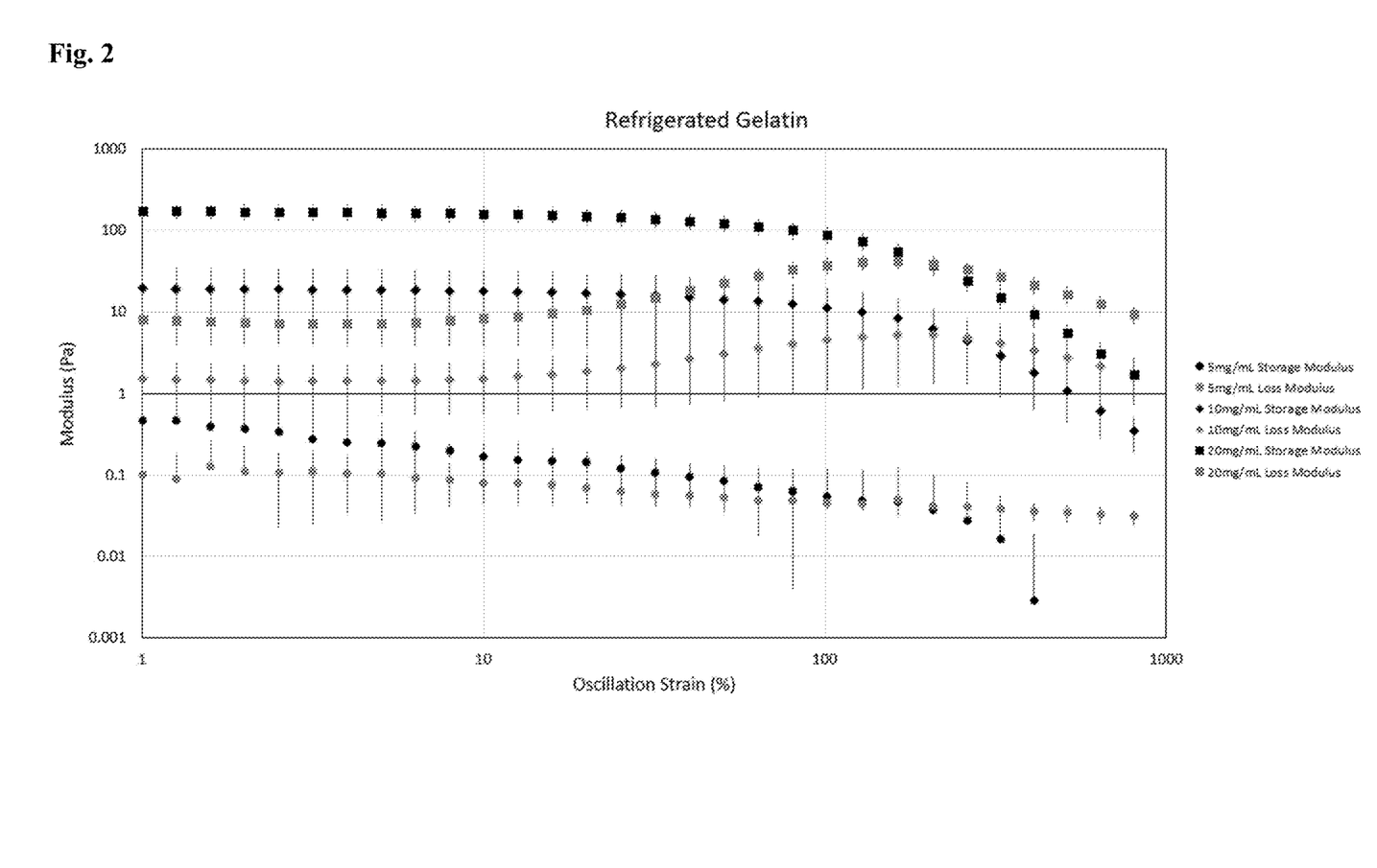
FIG. 2 is a graph of rheology data for gelatin solutions at concentrations of 5 mg/mL, 10 mg/mL, or 20 mg/mL.

Rheology data was collected on gelatin solutions having gelatin concentrations of 5 mg/mL, 10 mg/mL, or 20 mg/mL used for immersion printing. The results are shown in FIG. 2. Rheology data was collected at 4° C. using a 25 mm 2° cone and plate. The 20 mg/mL gelatin solution was too stiff of a solid as shown by magnitude of, and difference between, G' and G". The 5 mg/mL solution was a liquid, too loose for this application. The 10 mg/mL was a soft solid, in between the other two.

Example 3

Figure 3:
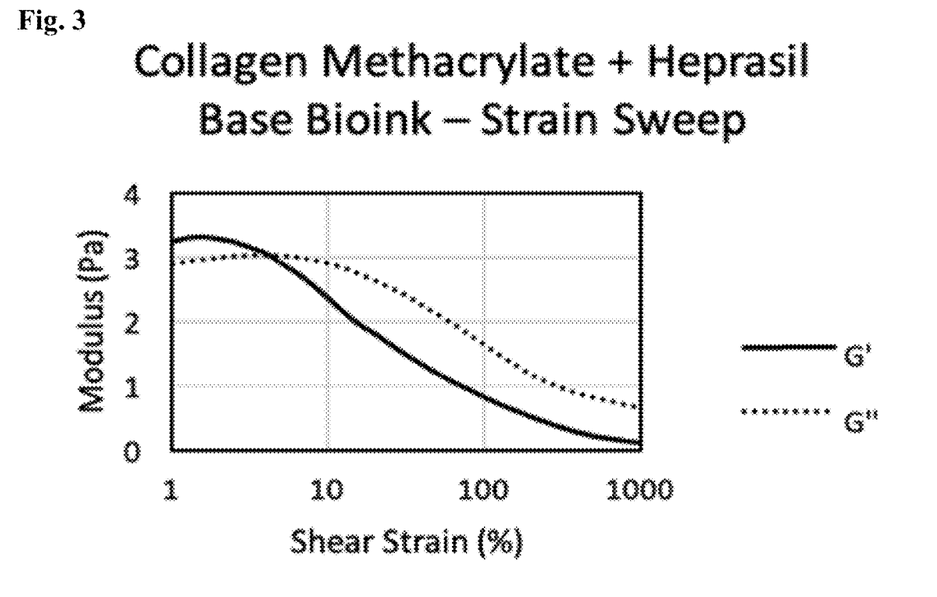
FIG. 3 is a graph showing strain sweep for a bioink according to some embodiments of the present invention.

Organoids were printed into different gelatin compositions having gelatin concentrations of 5 mg/mL, 10 mg/mL, or 20 mg/mL as described above in Example 2. The bioink used to print the organoids included collagen, methacrylate, and HEPRASIL® (thiol-modified hyaluronic acid with thiol-modified heparin) and had an elastic modulus that was between 3 and 4 Pa at low strain as shown in FIG. 3.

Figure 4:
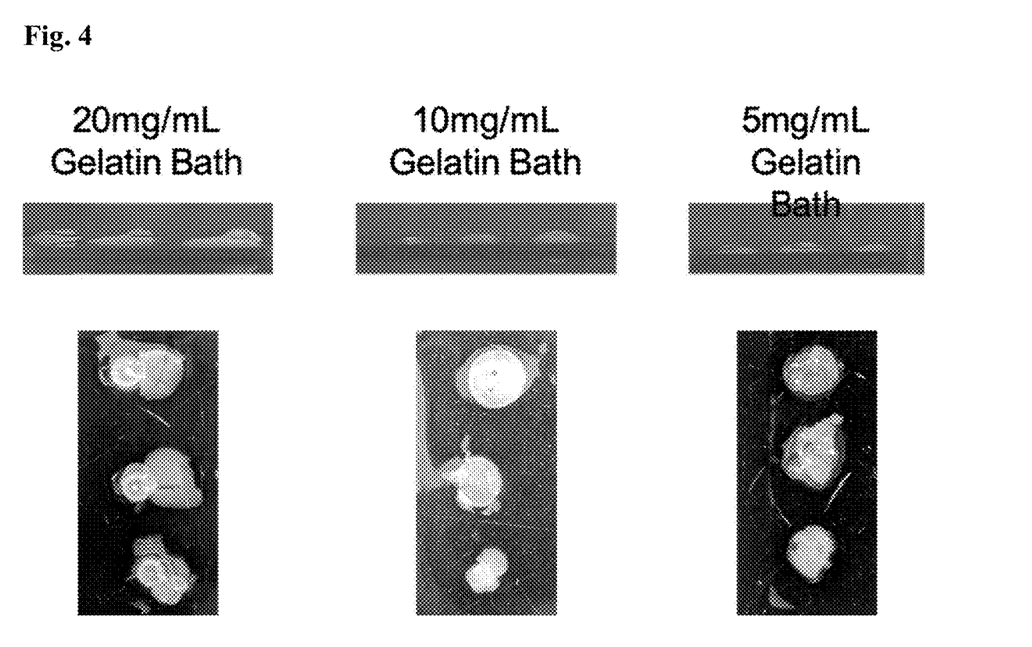
FIG. 4 is an image of organoids prepared by an immersion printing method with gelatin compositions having gelatin concentrations of 5 mg/mL, 10 mg/mL, or 20 mg/mL.

The 5 mg/mL gelatin composition produced inconsistent organoids that were similar to cotton balls as shown in FIG. 4. This is due to the bioink diffusing into the liquid gelatin composition, and then being cured. The 10 mg/mL gelatin composition produced organoids that were between spheres and thick disks as shown in FIG. 4. This gelatin composition was still a solid, and still a little stiff, which caused the gelatin composition to squish the organoid a little bit, creating a thick disk instead of a sphere. The 20 mg/mL gelatin composition produced a dual morphology of a thin disk attached to a spheroid as shown in FIG. 4. The gelatin composition was so stiff that it squished all of the bioink out once the printing needle was removed. The bioink left in the gelatin solution produced a thin disk. The bioink that was pushed out forms a spheroid on top of the gelatin composition which is connected to the thin disk.

Example 4

Primary sarcoma cells were isolated from donor tissue, expanded in culture, and processed into organoids, at 4 million cells per mL, using the base bioink formulation of Example 3, which was: 6 mg/mL methacrylated collagen mixed with 10 mg/mL HEPRASIL® (thiol-modified hyaluronic acid with thiol-modified heparin) in a 3:1 ratio and included 1 mg/mL LAP photoinitiator and had an elastic modulus between 3 and 4 Pa at low strain as described above in Example 3. The organoids were made using an immersion printing technique using a gelatin composition having a gelatin concentration of 10 mg/mL. To prepare the gelatin composition, gelatin was allowed to completely dissolve, and then the composition was cooled at 4° C. prior to use. The organoids were printed with a new bioprinter, BIO X™ available from CELLINK®, using a new type of printhead, a syringe pump printhead.

Figure 5:
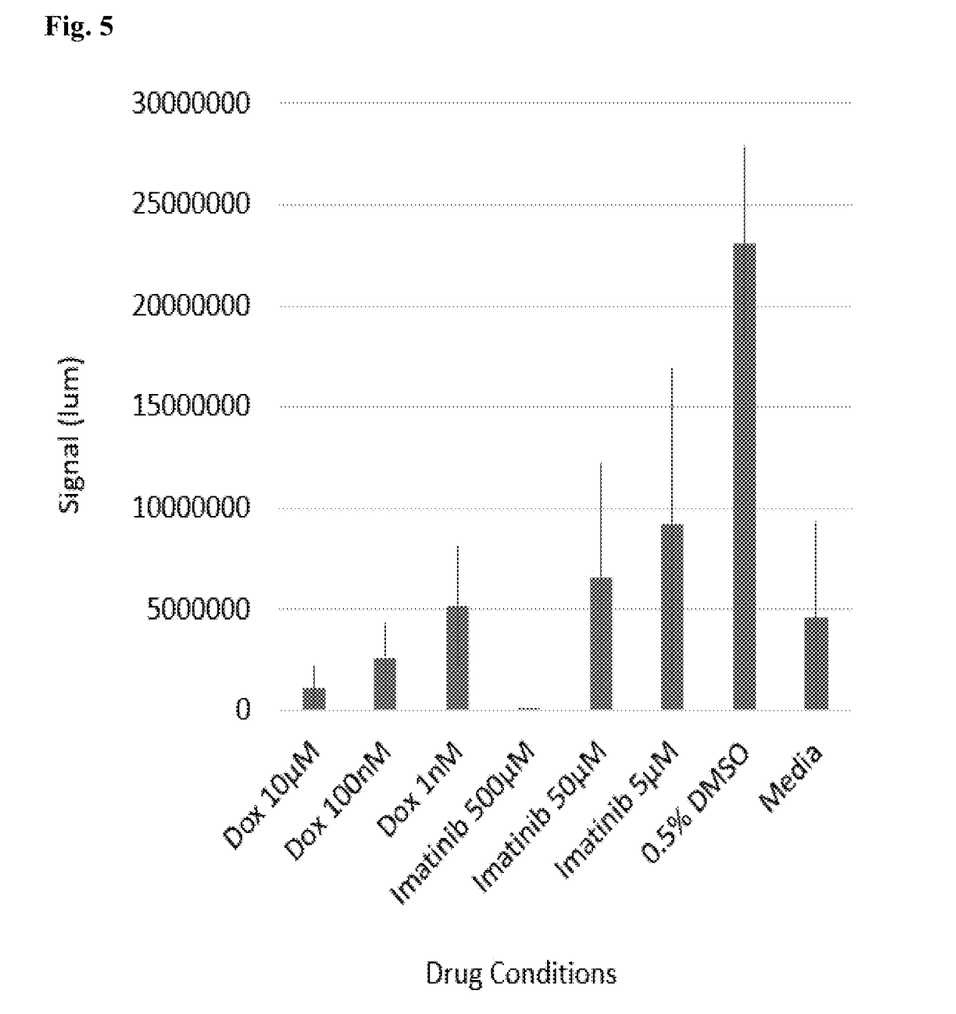
FIG. 5 is a graph showing the results from an ATP assay of drug treated primary sarcoma organoids.

The resulting organoids were cultured for 7 days, and then subjected to various drug conditions in culture for 3 more days. Table 1 details the drug and concentration added to the standard culture media (high glucose DMEM supplemented with 10% fetal bovine serum, 1% L-glutamine, 1% penicillin/streptomycin). The organoids were then measured for viability using the CELLTITER-GLO® 3D ATP assay to measure ATP content via luminescence. The resulting signals, shown in FIG. 5, show a trend of organoid viability decreasing as drug concentration increased. Live/dead imaging corroborates the findings of the ATP assay.

TABLE 1

Drug concentrations and resulting ATP assay signal.

|  | AVG Signal (lum) | SD Signal |
| --- | --- | --- |
| Doxorubicin 10 µM | 1.12E+06 | 1.06E+06 |
| Doxorubicin 100 nM | 2.62E+06 | 1.65E+06 |
| Doxorubicin 1 nM | 5.13E+06 | 3.06E+06 |
| Imatinib 500 µM | 1.88E+04 | 1.02E+04 |
| Imatinib 50 µM | 6.56E+06 | 5.64E+06 |
| Imatinib 5 µM | 9.16E+06 | 7.77E+06 |
| 0.5% DMSO | 2.30E+07 | 4.85E+06 |
| Media | 4.56E+06 | 4.75E+06 |
| Blank | 1.29E+03 | 4.01E+02 |

Overall, this study demonstrates that this printing platform can be used with the immersion printing technique, and that the immersion printing technique can be used with primary cancer cells.

The foregoing is illustrative of the present invention, and is not to be construed as limiting thereof. The invention is defined by the following claims, with equivalents of the claims to be included therein. All publications, patent applications, patents, patent publications, and other references cited herein are incorporated by reference in their entireties for the teachings relevant to the sentence and/or paragraph in which the reference is presented.

That which is claimed is:

1. A method of depositing a plurality of cells into a reservoir, the method comprising:
   depositing a gelatin composition into a reservoir, wherein the gelatin composition is a solution and gelatin is dissolved in the gelatin composition;
   adding a composition comprising a plurality of cells into the gelatin composition, wherein the composition is added into the gelatin composition at a position below the surface of the gelatin composition and at least a portion of the composition and/or plurality of cells are suspended in the gelatin composition;
   curing at least a portion of the composition comprising the plurality of cells in the gelatin composition; and
   removing at least a portion of the gelatin composition in the reservoir, thereby depositing the plurality of cells in the reservoir,
   wherein the gelatin composition comprises gelatin at a concentration of about 1 mg/mL to about 15 mg/mL and, at 4° C., the gelatin composition has an elastic modulus of about 5 Pa to about 15 Pa at about 1% to about 100% strain, and
   wherein the composition comprising the plurality of cells, at 4° C., has an elastic modulus of about 3 Pa to about 4 Pa at 1%-10% strain and the elastic modulus of the composition comprising the plurality of cells, at 4° C., is within an order of magnitude of the elastic modulus of the gelatin composition.

2. The method of claim 1, wherein the reservoir is a well in a 96-well plate or 384 well-plate.

3. The method of claim 1, wherein depositing the gelatin composition into the reservoir comprises depositing about 25 μL to about 350 μL of the gelatin composition into the reservoir.

4. The method of claim 1, wherein the gelatin composition has a viscosity prior to, during, and/or after deposition of about 0.01 Pascals*seconds (Pa·s) to about 20 Pa·s.

5. The method of claim 1, wherein adding the composition comprising the plurality of cells into the gelatin composition comprises extruding the composition into the gelatin composition using a syringe and/or printer.

6. The method of claim 1, wherein curing at least a portion of the composition comprising the plurality of cells comprises exposing at least a portion of the composition comprising the plurality of cells to light.

7. The method of claim 1, wherein removing at least a portion of the gelatin composition comprises adding a solution into the reservoir to wash away at least a portion of the gelatin composition.

8. The method of claim 1, further comprising, after removing at least a portion of the gelatin composition, adding cell culture media into the reservoir comprising the plurality of cells.

9. The method of claim 1, further comprising performing a high throughput assay with the plurality of cells in the reservoir.

10. The method of claim 1, further comprising growing the plurality of cells in culture for one or more day(s).

11. The method of claim 1, wherein the method provides a take rate of at least 50%.

12. The method of claim 1, wherein the plurality of cells comprise at least 75% live cells based on the average number of cells in the reservoir at 1 week of culture.

13. A method of printing a plurality of organoids, the method comprising:
   depositing a gelatin composition into a plurality of reservoirs, wherein the gelatin composition is a solution and gelatin is dissolved in the gelatin composition;
   adding a composition comprising a plurality of cells into the gelatin composition in each reservoir of the plurality of reservoirs, wherein the composition is added into the gelatin composition at a position below the surface of the gelatin composition and at least a portion of the composition and/or plurality of cells are suspended in the gelatin composition;
   curing at least a portion of the composition comprising the plurality of cells in the gelatin composition to form an organoid in each reservoir; and
   removing at least a portion of the gelatin composition in the plurality of reservoirs, thereby providing the plurality of organoids,
   wherein the gelatin composition comprises gelatin at a concentration of about 1 mg/mL to about 15 mg/mL and, at 4° C., the gelatin composition has an elastic modulus of about 5 Pa to about 15 Pa at about 1% to about 100% strain, and
   wherein the composition comprising the plurality of cells, at 4° C., has an elastic modulus of about 3 Pa to about 4 Pa at 1%-10% strain and the elastic modulus of the composition comprising the plurality of cells, at 4° C., is within an order of magnitude of the elastic modulus of the gelatin composition.

14. The method of claim 13, wherein less than about 20% of the reservoirs are connected after adding the composition comprising the plurality of cells into the gelatin composition in each reservoir of the plurality of reservoirs.

15. The method of claim 13, wherein the plurality of organoids, on average, have a uniform diameter in at least one dimension.

16. The method of claim 13, wherein the plurality of organoids comprise at least 75% live cells based on the average number of cells in the plurality of organoids at 1 week of culture.

17. The method of claim 1, wherein the composition suspended in the gelatin composition is in a substantially spherical form.

18. The method of claim 1, wherein the gelatin in the gelatin composition is in a form consisting of dissolved gelatin.

19. The method of claim 13, wherein the gelatin in the gelatin composition is in a form consisting of dissolved gelatin.

* * * * *

UNITED STATES PATENT AND TRADEMARK OFFICE
CERTIFICATE OF CORRECTION

PATENT NO. : 11,993,785 B2
APPLICATION NO. : 16/533300
DATED : May 28, 2024
INVENTOR(S) : Skardal et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1010 days.

Signed and Sealed this
Fifteenth Day of October, 2024

Katherine Kelly Vidal
*Director of the United States Patent and Trademark Office*